US010167516B2

(12) United States Patent
Newton et al.

(10) Patent No.: US 10,167,516 B2
(45) Date of Patent: Jan. 1, 2019

(54) SIX-GENE BIOMARKER OF SURVIVAL AND RESPONSE TO PLATINUM BASED CHEMOTHERAPY IN SERIOUS OVARIAN CANCER PATIENTS

(71) Applicants: Wisconsin Alumni Research Foundation, Madison, WI (US); The Medical College of Wisconsin, Inc., Milwaukee, WI (US)

(72) Inventors: Christina Kendziorski Newton, Madison, WI (US); Kevin Hasegawa Eng, Williamsville, NY (US); Janet S. Rader, Whitefish Bay, WI (US); William H. Bradley, Wauwatosa, WI (US)

(73) Assignee: Wisconsin Alumni Research Foundation, Madison, WI (US)

( * ) Notice: Subject to any disclaimer, the term of this patent is extended or adjusted under 35 U.S.C. 154(b) by 0 days.

(21) Appl. No.: 15/339,109

(22) Filed: Oct. 31, 2016

(65) Prior Publication Data
US 2017/0044627 A1 Feb. 16, 2017

Related U.S. Application Data

(63) Continuation of application No. 14/250,854, filed on Apr. 11, 2014.
(60) Provisional application No. 61/813,911, filed on Apr. 19, 2013.

(51) Int. Cl.
| | |
|---|---|
| *C12Q 1/68* | (2018.01) |
| *C12Q 1/6886* | (2018.01) |
| *G01N 33/574* | (2006.01) |
| *A61K 31/138* | (2006.01) |
| *A61K 31/337* | (2006.01) |
| *A61K 31/4745* | (2006.01) |
| *A61K 31/519* | (2006.01) |
| *A61K 31/704* | (2006.01) |
| *A61K 31/7068* | (2006.01) |
| *A61K 33/24* | (2006.01) |
| *A61K 39/395* | (2006.01) |

(52) U.S. Cl.
CPC .......... *C12Q 1/6886* (2013.01); *A61K 31/138* (2013.01); *A61K 31/337* (2013.01); *A61K 31/4745* (2013.01); *A61K 31/519* (2013.01); *A61K 31/704* (2013.01); *A61K 31/7068* (2013.01); *A61K 33/24* (2013.01); *A61K 39/3955* (2013.01); *G01N 33/57449* (2013.01); *C12Q 2600/118* (2013.01); *C12Q 2600/156* (2013.01); *C12Q 2600/158* (2013.01); *C12Q 2600/178* (2013.01); *G01N 2800/50* (2013.01); *G01N 2800/52* (2013.01)

(58) Field of Classification Search
None
See application file for complete search history.

(56) References Cited

U.S. PATENT DOCUMENTS

2010/0137149 A1   6/2010   Shin et al.

OTHER PUBLICATIONS

Bell, et al., The Cancer Genome Atlas Research Network, Integrated genomic analysis of ovarian carcinoma, Nature, 2011, 474, 609-615.
Berchuck, et al., Patterns of gene expression that characterize long-term survival in advanced stage serous ovarian cancers, Clin. Cancer Res., 2005, 11(10), 3686-3696.
Bild, et al., Oncogenic pathway signatures in human cancers as a guide to targeted therapies, Nature, 2006, 439, 353-357.
Choi, et al., IPI59: an actionable biomarker to improve treatment response in serous ovarian carcinoma patients, Statistics in Bioscience, 2016.
Crijns, et al., Survival-related profile, pathways, and transcription factors in ovarian cancer, PLoS Medicine, 2009, 6(2), e1000024.
Denkert, et al., A prognostic gene expression index in ovarian cancer-validation across different independent data sets, Journal of Pathology, 2009, 218, 273-280.
Dressman, et al., An integrated genomic-based approach to individualized treatment of patients with advanced-stage ovarian cancer, Journal of Clinical Oncology, 2007, 25(5), 517-525.
Eng, et al., Pathway index models for construction of patient-specific risk profiles, Statistics in Medicine, 2012.
Irizarry, et al., Exploration, normalization and summaries of high density oligonucleotide array probe level data, Biostatistics, 2003, 4(2), 249-264.
Jones, et al., Core signaling pathways in human pancreatic cancers revealed by global genomic analyses, Science, 2008, 321, 1801-1806.
Jones, et al., Pathways to cancer therapy, Nature Reviews Drug Discovery, 2008, 7, 875-876.
Kanehisa, et al., KEGG: Kyoto encyclopedia of genes and genomes, Nucleic Acids Research, 2000, 28(1), 27-30.
Marchion, et al., BAD phosphorylation determines ovarian cancer chemosensitivity and patient survival, Clinical Cancer Research, 2011, 17(19), 6356-6366.
Rosewald, et al., The use of molecular profiling to predict survival after chemotherapy for diffuse large-B-cell lymphoma, The New England Journal of Medicine, 2002, 346(25), 1937-1947.

(Continued)

*Primary Examiner* — Jehanne S Sitton
(74) *Attorney, Agent, or Firm* — Quarles & Brady LLP

(57) ABSTRACT

Described herein are methods of predicting the risk of developing ovarian cancer recurrence of a subject comprising the steps of detecting the expression levels of at least four of the six genes selected from the group consisting of AKT2, KRAS, RAC1, CALM3, RPS6KA2 and YWHAB or the gene products thereof, wherein the presence of increased expression levels of the genes or the gene products is predictive of the increased risk of developing ovarian cancer recurrence in the subject. Kits for practicing the methods are also disclosed.

10 Claims, 8 Drawing Sheets

(56) References Cited

OTHER PUBLICATIONS

Segel, R. A., Selectivity in neurotrophin signaling: Theme and variations, Annual Review of Neuroscience, 2003, 26, 299-330.
Siegel, et al., Cancer statistics, 2013, Ca Cancer J Clin, 2013, 63, 11-30.
Sparano, et al., Development of the 21-gene assay and its application in clinical practice and clinical trials, Journal of Clinical Oncology, 2008, 26, 721-728.
Tothill, et al., Novel molecular subtypes of serous and endometrioid ovarian cancer linked to clinical outcome, Clin Cancer Res., 2008, 14(16), 5198-5208.
Vaughan, et al., Rethinking ovarian cancer: Recommendations for Improving Outcomes, Nat Rev Cancer, 2012, 11(10), 719-725.
Verhaak, et al., Prognostically relevant gene signatures of high-grade serous ovarian carcinoma, The Journal of Clinical Investigation, 2013, 123(1), 517-252.
Vogelstein, et al., Cancer genes and the pathways they control, Nature Medicine, 2004, 10(8), 789-799.
Yoshihara, et al., Gene expression profile for predicting survival in advanced-stage serous ovarian cancer across two independent datasets, PLoS One, 2010, 5(3), e9615.
Wang, et al. Cancer Research, vol. 61, pp. 4169-4174, 2003.

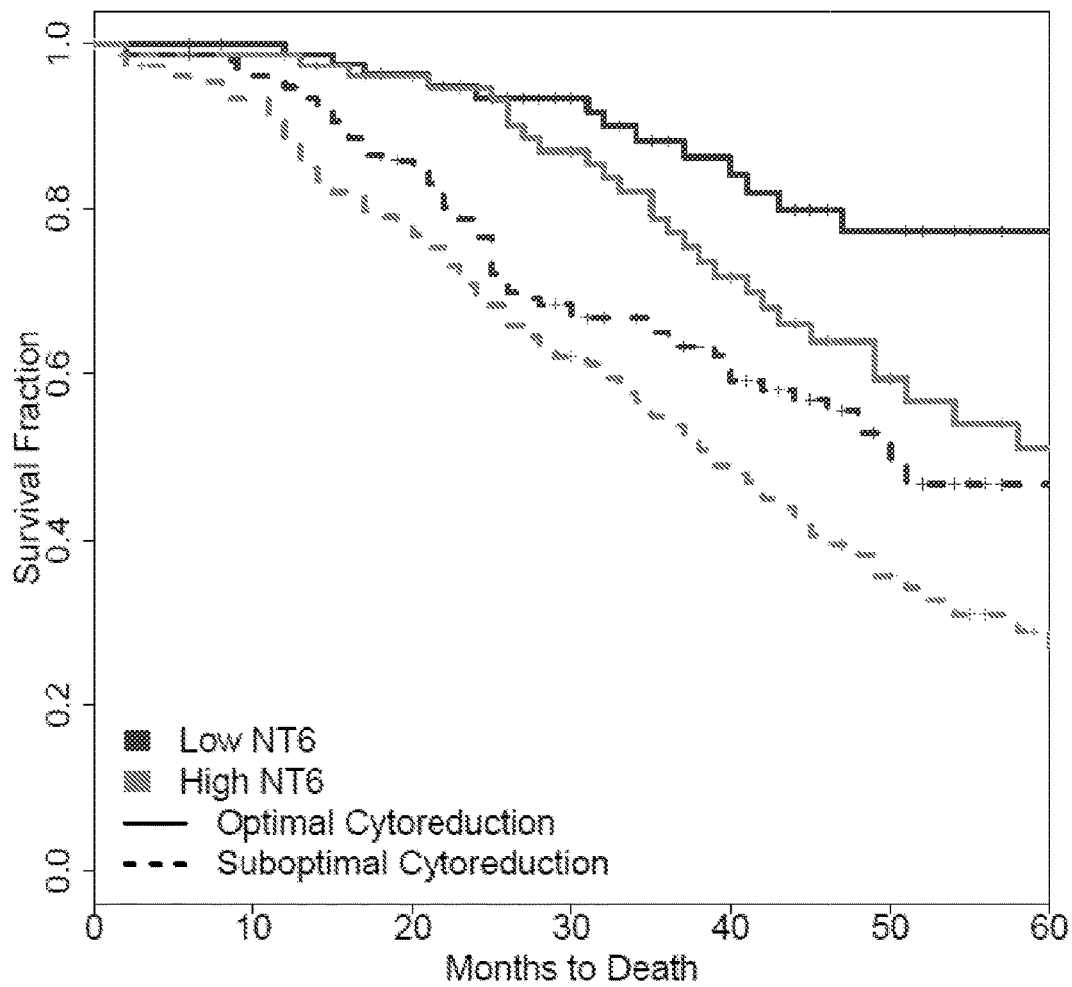

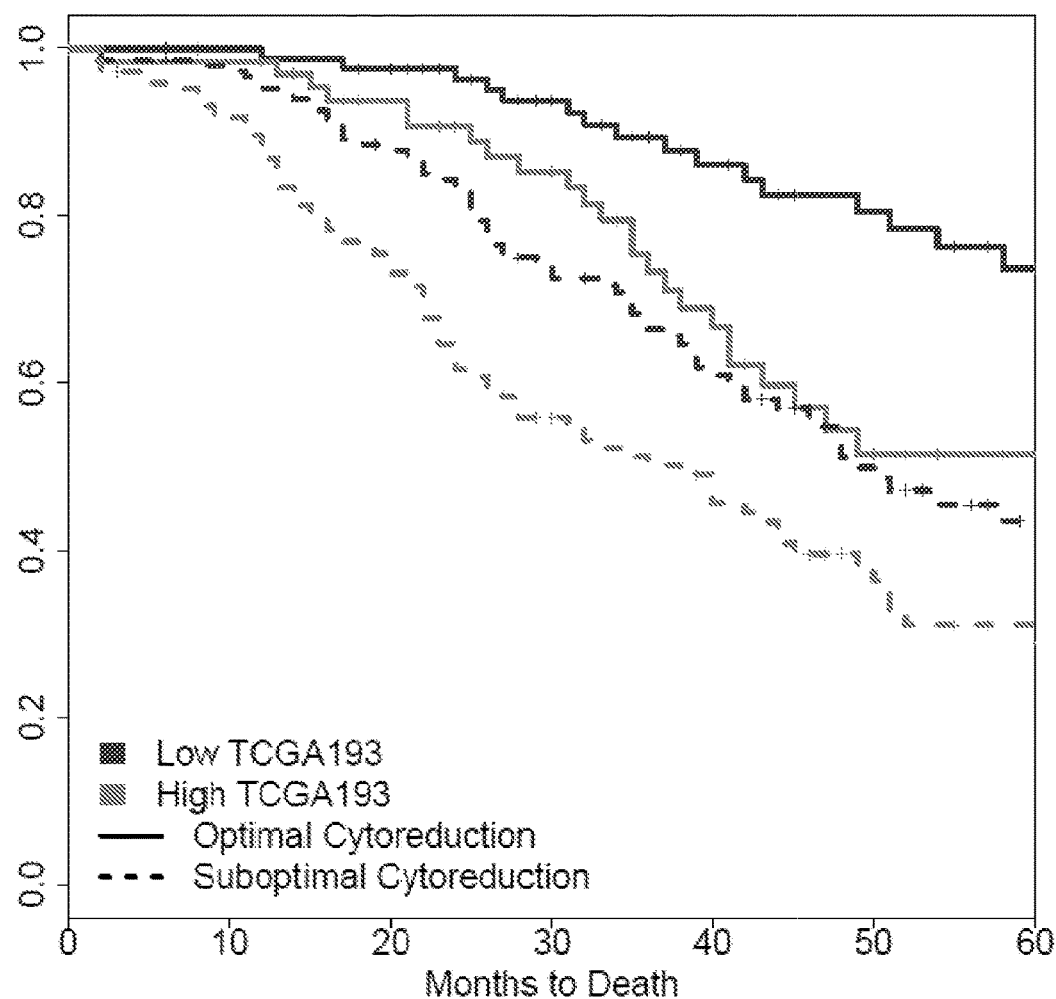

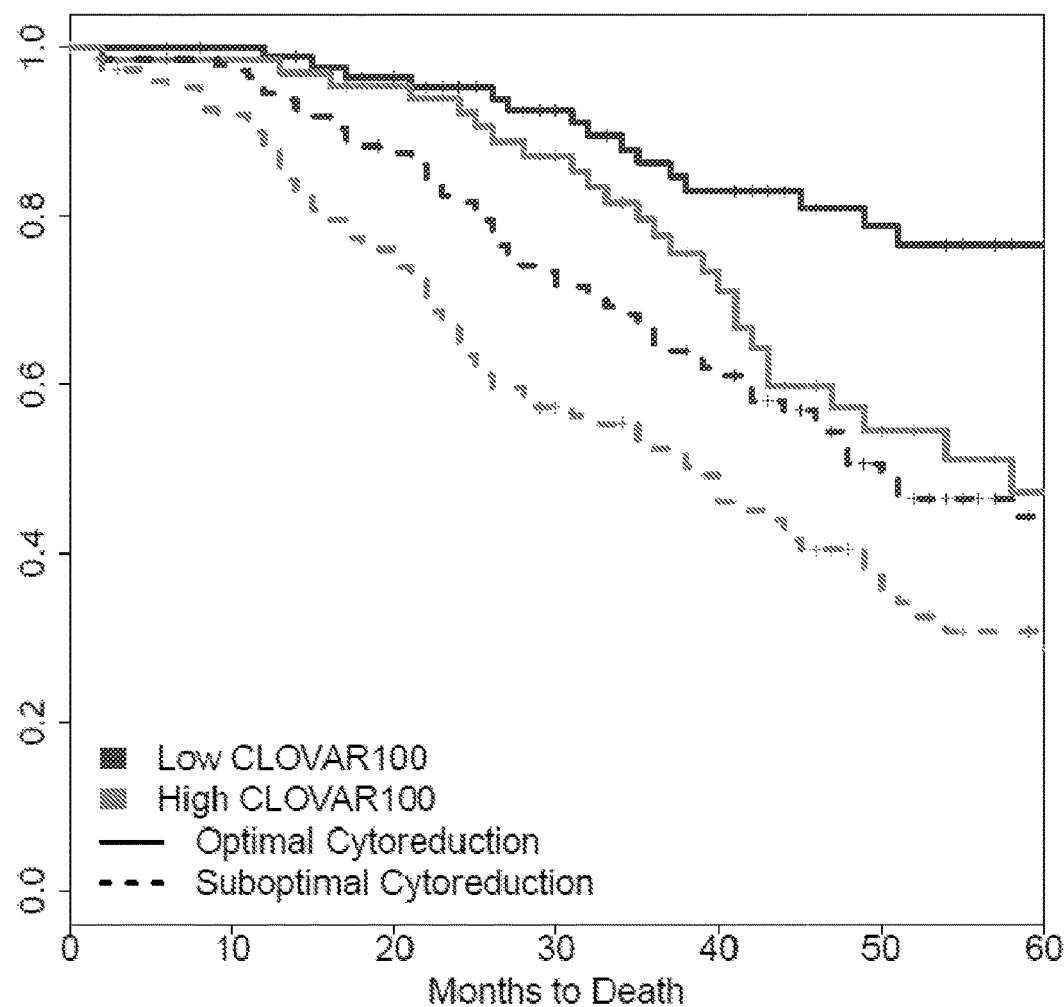

SIX-GENE BIOMARKER OF SURVIVAL AND RESPONSE TO PLATINUM BASED CHEMOTHERAPY IN SERIOUS OVARIAN CANCER PATIENTS

CROSS-REFERENCE TO RELATED APPLICATIONS

This application is a continuation of U.S. patent application Ser. No. 14/250,854, filed on Apr. 11, 2014, which claims the benefit of U.S. Provisional Patent Application Ser. No. 61/813,911 filed on Apr. 19, 2013, each of which is incorporated herein by reference in its entirety for all purposes.

STATEMENT REGARDING FEDERALLY SPONSORED RESEARCH OR DEVELOPMENT

This invention was made with government support under GM102756 awarded by the National Institutes of Health. The government has certain rights in the invention.

BACKGROUND OF THE INVENTION

Epithelial ovarian cancer is the leading cause of gynecologic cancer death, accounting for over 14,000 deaths annually in the United States alone. Early diagnosis is difficult, and consequently most patients present at advanced stage (III or IV) where standard treatment is surgical debulking followed by a platinum-based chemotherapy. Most patients with advanced ovarian cancer (AOC) or high-grade ovarian cancer do not achieve a sustainable response under standard of care, and over 60% recur within two years. There are a number of agents available to treat recurrence, but how to choose the most beneficial one is not clear. The ability to identify patients at high-risk for early recurrence (and/or shortened survival) and accurately predict their optimal treatment is needed if we are to improve AOC patient survival in a meaningful way.

A number of methods are available for identifying patients at high-risk for early recurrence or death. Residual disease after surgical cytoreduction is the measure most widely used in clinical practice. It has been associated with both overall and progression free survival in numerous studies, with age, grade, and CA-125 levels improving predictions slightly. Although useful for prognostic purposes, these measures do not provide information to guide treatment. Genomic and proteomic prognostic markers have also been developed, and a few have been associated with pathways that suggest candidate therapies. In spite of these advances, the ability to identify recurrent patients who may benefit from select therapies remains elusive.

SUMMARY OF THE INVENTION

The present invention relates to using the expression level of six specific genes to predict the risk of developing ovarian cancer recurrence and/or assess the effectiveness of a chemotherapeutic treatment for ovarian cancer.

In its first aspect, the present invention provides methods of predicting the risk of developing ovarian cancer recurrence in a subject comprising the steps of: (a) obtaining a sample from a subject; (b) analyzing the expression levels of at least four genes selected from the group consisting of AKT2, KRAS, RAC1, CALM3, RPS6KA2 and YWHAB or the gene products thereof in the sample, wherein the presence of increased expression levels of the genes or the gene products is predictive of increased risk of ovarian cancer recurrence in the subject; and (c) treating the subject with alternative therapies.

In its second aspect, the present invention provides methods of determining the effectiveness of a platinum-based therapy for a subject with ovarian cancer comprising the steps of: (a) obtaining a sample from a subject; (b) analyzing the expression levels of at least four genes selected from the group consisting of AKT2, KRAS, RAC1, CALM3, RPS6KA2 and YWHAB or the gene products thereof in the sample, wherein the presence of increased expression levels of the genes or the gene products is predictive of increased resistance to platinum-based therapy in the subject; and (c) treating the subject with alternative therapies.

In certain embodiments, the alternative therapy is selected from the group consisting of treatment with taxane, bevacizumab, docetaxel, doxorubicin, gemcitabine, pemetrexed, tamoxifen, topotecan and mixtures thereof. Preferably, the alternative therapy is used with platinum or taxane.

In its third aspect, the present invention provides kits for predicting the risk of developing ovarian cancer recurrence of a subject comprising: (a) at least one reagent that is capable of detecting the expression levels of at least four genes selected from the group consisting of AKT2, KRAS, RAC1, CALM3, RPS6KA2 and YWHAB or the gene products thereof in a patient sample; wherein the presence of increased expression of levels of the genes or the gene products is predictive of the increased risk of ovarian cancer recurrence in the subject.

In its fourth aspect, the present invention provides kits for determining the resistance to a platinum-based therapy for a subject with ovarian cancer comprising: (a) at least one reagent capable of detecting the expression levels of at least four genes selected from the group consisting of AKT2, KRAS, RAC1, CALM3, RPS6KA2 and YWHAB or the gene products thereof in a sample, wherein the presence of increased expression levels of the genes or the gene products is predictive of increased resistance to the platinum-based therapy in the subject.

In certain embodiments, the reagent in the kits comprises antibodies immunologically specified for the proteins encoded by the genes, and preferably used in an ELISA.

In certain embodiments, the reagent comprises probes complementary to the genes, and preferably the primers complementary to the genes.

In its fifth aspect, the present invention provides methods of diagnosing the risk of developing ovarian cancer recurrence of a subject comprising the steps of: (a) obtaining a sample from a subject; and (b) analyzing the expression levels of at least four genes selected from the group consisting of AKT2, KRAS, RAC1, CALM3, RPS6KA2 and YWHAB or the gene products thereof in the sample, wherein the presence of increased expression of level of the genes or the gene products is predictive of increased risk of ovarian cancer recurrence in the subject.

In its sixth aspect, the present invention provides methods of amplifying at least four of six target gene sequences comprising the steps of (a) providing a reaction mixture comprising a double-stranded target DNA, wherein the DNA is obtained from a subject, and (i) at least one pair of primers selected from the group designed to amplify at least four genes selected from the group consisting of target genes AKT2, KRAS, RAC1, CALM3, RPS6KA2 and YWHAB, wherein the primer pair comprises a first and a second primer that are complementary to the target DNA sequence, (ii) a polymerase and (iii) a plurality of free nucleotides comprising adenine, thymine, cytosine and guanine; (b)

heating the reaction mixture to a first predetermined temperature for a first predetermined time to separate the strands of the target DNA from each other; (c) cooling the reaction mixture to a second predetermined temperature for a second predetermined time under conditions to allow the first and second primers to hybridize with their complementary sequences on the target DNA and to allow the polymerase to extend the primers; and (d) repeating steps (b) and (c) at least 10 times.

In certain embodiments, PCR reaction buffer and $MgCl_2$ are additionally added to step (a) of the method.

In certain embodiments, the method additionally comprises the step of analyzing the products of step (e) to determine whether increased risk of ovarian cancer in the subject is indicated, and/or the step of analyzing the products of step (e) to determine whether the products are predictive of increased resistance to platinum-based cancer therapies.

In certain embodiments, the method additionally comprises the step of treating the subject with alternative therapies.

It should be understood that these and other features of the present invention will become apparent to the skilled artisan from the following detailed description considered in conjunction with the accompanying drawings.

BRIEF DESCRIPTION OF THE DRAWINGS

FIGS. 2A-2C show Kaplan-Meier curves showing percent survival for 501 validation patients stratified into four groups defined by cytoreduction status (complete vs. incomplete) and prognosis (low-risk vs. high-risk) from NT6 (A), TCGA193 (B), and CLOVAR100 (C).

DESCRIPTION OF THE INVENTION

In General

Figure 1:
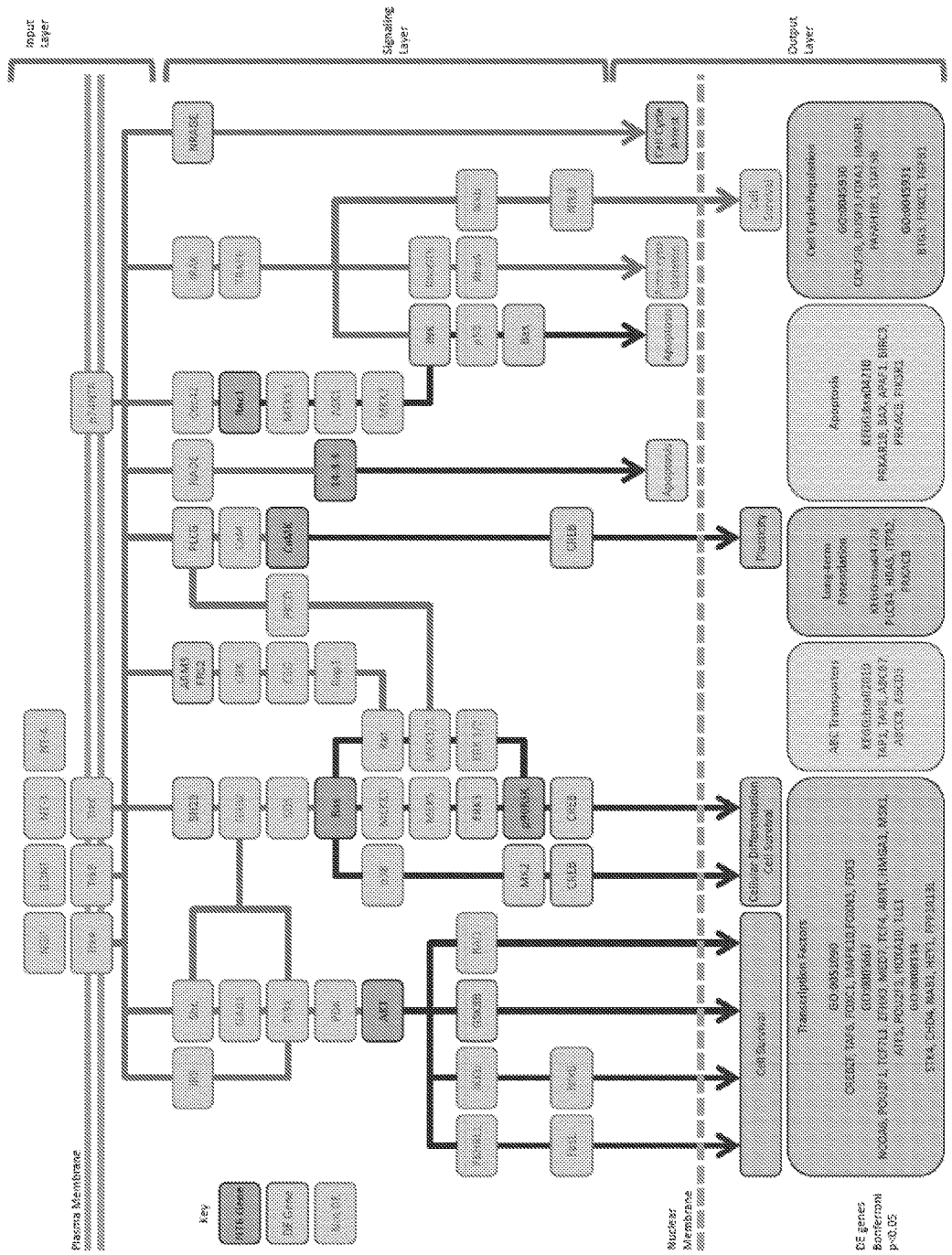
FIG. 1 shows Neurotrophin (NT) pathway signaling, reproduced from KEGG:hsa04722 and [9], is shown in the signaling layer; also shown are factors affecting (input layer) or affected by (output layer) NT signaling. Highlighted are the NT6 genes as well as genes found to be differentially expressed between low and high NT6 patients.

The present invention is based, at least in part, on the discovery that certain genes or biomarkers are associated with the increased risk of recurrence or early death of ovarian cancer patients. These biomarkers are detectable in biological samples from patients.

The term "patient" or "subject" refers to a female mammalian animal, including a human, a veterinary or farm animal, a domestic animal or pet, and animals normally used for clinical research, including non-human primates, dogs and mice. More specifically, the subject of the present invention is a female human.

The term "cancer" and "cancerous" refer to or describe the physiological condition in mammals that is typically characterized by unregulated cell growth. The term "cancer" as used herein includes carcinomas, (e.g., carcinoma in situ, invasive carcinoma, metastatic carcinoma) and pre-malignant conditions, neomorphic changes independent of their histological origin. In turn, the term "ovarian cancer" refers to any cancerous growth arising from the ovary, which includes, but is not limited to, traditionally diagnosed ovarian, fallopian tube and primary peritoneal cancers. In some embodiments, ovarian cancer is a type of cancer that forms in tissues of the ovary. In other embodiments, ovarian cancer is either ovarian epithelial carcinomas (cancer that begins in the cells on the surface of the ovary) or malignant germ cell tumors (cancer that begins in egg cells).

Also, the terms "cancer" and "ovarian cancer" are not limited to any stage, grade, histomorphological feature, invasiveness, aggressiveness or malignancy of an affected tissue or cell aggregation. In particular, cancer or ovarian cancer used herein includes stage 0 cancer, stage I cancer, stage II cancer, stage III cancer, stage IV cancer, grade I cancer, grade II cancer, grade III cancer, malignant cancer and/or primary carcinomas. Typically, Stage I of ovarian cancer is confined to one or both ovaries. The cancer is Stage II if either one or both of the ovaries is involved and has spread to the uterus and/or the fallopian tubes or other sites in the pelvis. The ovarian cancer is Stage III cancer if one or both of the ovaries is involved and has spread to lymph nodes or other sites outside of the pelvis but is still within the abdominal cavity, such as the surface of the intestine or liver. The ovarian cancer is Stage IV cancer if one or both ovaries is involved and has spread outside the abdomen or has spread to the inside of the liver.

In some embodiments, the ovarian cancer patient is a subject who is asymptomatic for ovarian cancer. In some embodiments, the subject has shown clinical symptoms of ovarian cancer. In some embodiments, the subject has been diagnosed with ovarian cancer. In a preferred embodiment, the subject has advanced ovarian cancer, which means the cancer cells spread away from the ovary to other parts of the subject's body, typical characterized as Stage 2 to 4 cancer.

The term "cancer recurrence", in pathology nomenclature, refers to re-growth at the site of the primary tumor. In some embodiments, the cancer recurred after a period of time during which the cancer could not be detected, or after at least partial cancer tissues had been surgically removed, or after the growth of cancer cells were inhibited by therapeutic treatment. The cancer may reoccur on or come back to the same place as the original (primary) tumor or to another place in the body.

The term "likelihood" or "increased risk" refers to an increase in the risk or probability that the subject is not able to survive ovarian cancer for an expected period of time (early death), either due to development of ovarian cancer recurrence, or due to resistance to therapeutic treatment for ovarian cancer, or both. In some embodiments, the cancer recurrence is also associated with resistance to platinum and/or taxane based chemotherapies.

Thus, the term "likelihood of cancer recurrence" or "increased risk of cancer recurrence" herein means the risk of cancer recurrence in the body of a cancer patient or the risk of early death caused by cancer recurrence. Unless otherwise specified herein, the term "risk of recurrence"

includes either or both of the risks. In a preferred embodiment, the likelihood means an increased risk of ovarian cancer recurrence.

The term "sample" or "biological sample" refers to a sample obtained from a subject. The sample may be of any biological tissue or fluid. Such samples include, but are not limited to, sputum, blood, serum, plasma, blood cells (e.g., white cells), tissue including tumor tissue, core or fine needle biopsy samples, cell-containing body fluids, free floating nucleic acids, urine, peritoneal fluid, and pleural fluid, or cells there from. Biological samples may also include sections of tissues such as frozen or fixed sections taken for histological purposes or microdissected cells or extracellular parts thereof. For example, in some specific embodiments, the sample is a body fluid. Such fluids include, for example, blood fluids, serum, plasma, lymph, ascitic fluids, gynecological fluids, or urine but not limited to these fluids.

The term "biomarker" or "marker" refers to an organic biomolecule which is differentially present in a sample taken from a subject of one phenotypic status as compared with another phenotypic status. A biomarker is differentially present between different phenotypic statuses if the difference in the mean or median expression levels of the biomarker in the different groups is calculated to be statistically significant. Biomarkers, alone or in combination, provide measures of relative risk that a subject belongs to one phenotypic status or another. For the purpose of this invention, biomarkers are the markers for predicting or detecting the risk of ovarian cancer recurrence. In some embodiments, the biomarkers are the genes disclosed herein. In some other embodiments, the biomarkers are the product of the genes.

Embodiments of the Invention

Embodiments of the present invention relate to methods and kits for predicting or assessing the risk of ovarian cancer recurrence in a subject by using biomarkers disclosed herein.

Specifically, we applied the pathway-index model to mRNA expression and survival data collected on ovarian cancer patients as part of the Cancer Genome Atlas (TCGA) project (Kevin H. Eng, Sijian Wang, William H. Bradley, Janet S. Rader, and Christina Kendziorski. Pathway index models for construction of patient-specific risk profiles. *Statistics in Medicine,* 2012, 32(9): 1524-1535). For a given collection of genes specified a priori, the pathway-index model uses expression measured in a population of patients to identify susceptibility (resistance) genes conferring increased (decreased) risk of a time-to-event phenotype such as recurrence or early death.

A patient-specific summary of risk, called an index, is then constructed using each patient's expression profile at the selected genes. After a search over 229 KEGG pathways (including metabolic and disease specific pathways as negative controls), we identified six genes (AKT2, KRAS, RAC1, CALM3, RPS6KA2, YWHAB) in the neurotrophin growth factor pathway (KEGG:hsa04722) whose overexpression is significantly associated with poor overall survival. We refer to these six genes hereinafter as NT6.

We also found that NT6 is also significantly associated with platinum resistance and may be used to identify patients who are likely to respond to augmented adjuvant therapy. Moreover, we found that NT6 is associated with patient-specific response to therapy in recurrent AOC patients with high sensitivity and specificity. Therefore, it is envisioned that NT6 can serve as a basis of clinically useful prognostic and predictive biomarkers.

Thus, in its first aspect, the present invention relates to a method of predicting the risk of developing ovarian cancer recurrence of a subject comprising the steps (a) obtaining a sample from a subject, (b) analyzing the expression levels of at least four genes selected from the group consisting of AKT2, KRAS, RAC1, CALM3, RPS6KA2 and YWHAB or the gene products thereof in the sample, wherein the presence of increased expression levels of the genes or gene products is predictive of the increased risk of developing ovarian cancer recurrence in the subject.

In its second aspect, the present invention relates to a method of determining the effectiveness of adjuvant therapy for a subject with ovarian cancer comprising the steps (a) obtaining a sample from a subject, (b) analyzing the expression levels of at least four genes selected from the group consisting of AKT2, KRAS, RAC1, CALM3, RPS6KA2 and YWHAB or the gene products thereof in the sample, wherein the presence of increased expression levels of the genes or gene products is predictive of the increased resistance to adjuvant therapy in the subject. Because adjuvant treatments for ovarian cancer are universally platinum-based, this method is preferred to determining the effectiveness of platinum-based therapy for a subject with ovarian cancer.

In some embodiments, the expression levels of the genes or the gene products thereof are compared to those of a control group. A control group may be the same patient before ovarian cancer or ovarian cancer recurrence, or a different patient who does not suffer from a risk of ovarian cancer or ovarian cancer recurrence, or a different patient who has a relatively lower risk of ovarian cancer or ovarian cancer recurrence, or a healthy patient or group of patients. Various comparison strategies exist in the art and any of them can be used for the purpose of this invention. For example, one strategy is to compare the expression of biomarkers with the normalized expression of these the genes in the patient and/or a control group.

In some embodiments, the increased expression of at least four genes selected from group consisting of AKT2, KRAS, RAC1, CALM3, RPS6KA2 and YWHAB indicates high risk of ovarian cancer recurrence or early death.

In some embodiments, the increased expression of at least five genes selected from group consisting of AKT2, KRAS, RAC1, CALM3, RPS6KA2 and YWHAB indicates high risk of ovarian cancer recurrence or early death.

In some other embodiments, the increased expression of all six genes selected from group consisting of AKT2, KRAS, RAC1, CALM3, RPS6KA2 and YWHAB indicates high risk of ovarian cancer recurrence or early death.

Any combination of 4, 5 or 6 genes disclosed herein is sufficient for carrying out the purpose of this invention. Also, the genes, combination of the genes, or number of genes used for predicting the risk of ovarian cancer recurrence, may vary upon specific patients. For example, as described in the Examples below, the patients of the study were separated into seven groups, with each group showing a distinct expression signature. Patients in the first group, for example, have relatively high expression of CALM3; patients in the second group have relatively high expression of YWHAB. Furthermore, each group contains high NT6 patients indicating that high NT6 is not driven by a single factor common across patients.

By reading the description of the invention, especially the Examples, one skilled in the art would understand how to determine or assess the risk of cancer recurrence for a specific patient, either by solely relying on expression results of the genes or by combining the results with other factors known in the art, for example, the patient's physical condition or clinical history.

One may determine the risk based on an average of, or any other functions, for example, without limitation, weighted average, median, multiplication, division, linear extrapolation, addition and substraction, applied to the expression levels of any four, five and all of the six NT6 genes descried above. Preferably, an average of the expression levels of at least four or five NT6 genes is used, and more preferably, an average of the expression levels of the six NT6 genes is used for determining the risk.

In some embodiments, the methods further comprise a step of managing treatment for a subject, especially for the subject who has been identified with an increased risk of ovarian cancer recurrence. The treatment can be either therapeutic, prophylactic or preventative, wherein the object is to prevent or slow down the targeted pathologic condition or disorder, in particular the conditions associated with ovarian cancer recurrence. For example, the expression levels of biomarkers disclosed herein may indicate resistance to the therapy that the subject received. Based on assessment results, one skilled in the art may determine whether the subject should be treated with an alternative therapy. In some other embodiments, the expression levels of the biomarkers may indicates the risk of early death. Based on assessment results, the patients may be managed to have their cancer progression monitored more frequently or receive suitable treatment.

In its third aspect, the present invention relates to a kit for predicting the risk of developing ovarian cancer recurrence of a subject comprising at least one reagent that is capable of detecting the expression levels of at least four genes selected from the group consisting of AKT2, KRAS, RAC1, CALM3, RPS6KA2 and YWHAB or the gene products thereof in a sample, wherein the presence of increased expression levels of the genes or the gene products is predictive of the increased risk of developing recurring ovarian cancer in the subject.

In its fourth aspect, the present invention relates to a kit of determining the effectiveness of adjuvant therapy for a subject with ovarian cancer comprising at least one reagent that is capable of detecting the expression levels of at least four genes selected from the group consisting of AKT2, KRAS, RAC1, CALM3, RPS6KA2 and YWHAB or the gene products thereof in a sample, wherein the presence increased expression levels of the genes or the gene products is predictive of the increased resistance to the adjuvant therapy in the subject. Preferably, the adjuvant therapy is a platinum-based therapy.

Generally, the reagent can be any molecules that are capable of binding the genes or the gene products and providing detectable measurement. The examples of reagents include, but are not limited to chemical compounds including organic or inorganic compounds, antibodies, single or double stranded oligonucleotides, amino acids, proteins, peptides or fragments thereof.

In some embodiments, the reagent comprises probes complementary to the genes. In some embodiments, the reagent comprises primers complementary to the genes. In some embodiments, the reagent comprises antibodies specifically binding to the peptide products of the genes. In some other embodiments, the reagent is the antibodies used in an ELISA.

The techniques for preparing and using the reagents according to the present invention are described below.

In its fifth aspect, the present invention also provides a method of inhibiting cancer cell growth but not re-sensitizing the cancer cells to platinum-based adjuvant therapy comprising the step of interrupting the expression of at least four genes selected from the group consisting of AKT2, KRAS, RAC1, CALM3, RPS6KA2 and YWHAB. Preferably, the interruption is inhibition.

Description Of The Biomarkers

Six genes (NT6), including AKT2, KRAS, RAC1, CALM3, RPS6KA2 and YWHAB, are discovered and subsequently identified as biomarkers in accordance with the present invention.

AKT2 is one of 3 closely related serine/threonine-protein kinases (AKT1, AKT2 and AKT3) called the AKT kinase, and which regulate many processes including metabolism, proliferation, cell survival, growth and angiogenesis. This gene is a putative oncogene encoding a protein belonging to a subfamily of serine/threonine kinases containing SH2-like (Src homology 2-like) domains. The gene has been shown to be amplified and overexpressed in 2 of 8 ovarian carcinoma cell lines and 2 of 15 primary ovarian tumors. The sequence information of AKT2 can be found under the Ensembl accession number ENSG00000105221.

In one specific embodiment, the AKT2 gene of the present invention comprises AKT2 (Ensembl accession number ENSG00000105221) or contiguous portions thereof, or sequences at least 90%, at least 95%, at least 98%, or at least 99% identical to the sequence of Ensembl accession number ENSG00000105221 or the contiguous portions thereof.

KRAS gene belongs to a class of genes known as oncogenes. When mutated, oncogenes have the potential to cause normal cells to become cancerous. The KRAS gene is in the Ras family of oncogenes, which also includes two other genes: HRAS and NRAS. The proteins produced from these three genes are GTPases. These proteins play important roles in cell division, cell differentiation, and the self-destruction of cells (apoptosis). The sequence information of KRAS can be found under the Ensembl accession number ENSG00000133703.

In one specific embodiment, the KRAS gene of the present invention comprises KRAS (Ensembl accession number ENSG00000133703) or contiguous portions thereof, or sequences at least 90%, at least 95%, at least 98%, or at least 99% identical to the sequence of Ensembl accession number ENSG00000133703 or the contiguous portions thereof.

The RAC1 gene encodes protein GTPase which belongs to the RAS superfamily of small GTP-binding proteins. Members of this superfamily appear to regulate a diverse array of cellular events, including the control of cell growth, cytoskeletal reorganization, and the activation of protein kinases. Two transcript variants encoding different isoforms have been found for this gene. The sequence information of RAC1 can be found under the Ensembl accession number ENSG00000136238.

In one specific embodiment, the RAC1 gene of the present invention comprises RAC1 (Ensembl accession number ENSG00000136238) or contiguous portions thereof, or sequences at least 90%, at least 95%, at least 98%, or at least 99% identical to the sequence of Ensembl accession number ENSG00000136238 or the contiguous portions thereof.

The CALM3 gene encodes protein Calmodulin 3, which mediates the control of a large number of enzymes, ion channels and other proteins by Ca(2+). Among the enzymes to be stimulated by the Calmodulin-Ca(2+) complex are a number of protein kinases and phosphatases. Together with CEP110 and centrin, CALM3 is involved in a genetic pathway that regulates the centrosome cycle and progression through cytokinesis. The sequence information of CALM3 can be found under the Ensembl accession number ENSG00000160014.

In one specific embodiment, the CALM3 gene of the present invention comprises CALM3 (Ensembl accession number ENSG00000160014) or contiguous portions thereof, or sequences at least 90%, at least 95%, at least 98%, or at least 99% identical to the sequence of Ensembl accession number ENSG00000160014 or the contiguous portions thereof.

The RPS6KA2 gene encodes a member of the RSK (ribosomal S6 kinase) family of serine/threonine kinases. This kinase contains 2 non-identical kinase catalytic domains and phosphorylates various substrates, including members of the mitogen-activated kinase (MAPK) signaling pathway. The activity of this protein has been implicated in controlling cell growth and differentiation. Alternate transcriptional splice variants, encoding different isoforms, have been characterized. The sequence information of RPS6KA2 can be found under the Ensembl accession number ENSG00000071242.

In one specific embodiment, the PRS6KA2 gene of the present invention comprises PRS6KA2 (Ensembl accession number ENSG00000071242) or contiguous portions thereof, or sequences at least 90%, at least 95%, at least 98%, or at least 99% identical to the sequence of Ensembl accession number ENSG00000071242 or the contiguous portions thereof.

The YWHAB gene encodes a protein belonging to the 14-3-3 family of proteins, members of which mediate signal transduction by binding to phosphoserine-containing proteins. This highly conserved protein family is found in both plants and mammals. The encoded protein has been shown to interact with RAF1 and CDC25 phosphatases, suggesting that it may play a role in linking mitogenic signaling and the cell cycle machinery. Two transcript variants, which encode the same protein, have been identified for this gene. The sequence information of YWHAB can be found under the Ensembl accession number ENSG00000166913.

In one specific embodiment, the YWHAB gene of the present invention comprises YWHAB (Ensembl accession number ENSG00000166913) or contiguous portions thereof, or sequences at least 90%, at least 95%, at least 98%, or at least 99% identical to the sequence of Ensembl accession number ENSG00000166913 or the contiguous portions thereof.

For the purpose of this invention, biomarkers also include the gene products of the six genes (NT6) or contiguous portions thereof, or of the sequences at least 90%, at least 95%, at least 98%, or at least 99% identical to these genes. As used herein, the term "gene product" refers to the mRNA or polypeptide product that results from transcription and/or translation of the gene.

The term "contiguous portions of a sequence" as used herein refers to a non-interrupted sequence of nucleic acids or amino acids also occurring in the same order in the sequence referred to. Particularly envisaged are contiguous portions having a length of at least 25% 50% 0% 5% 80% or 90% of the length of the reference sequence, and contiguous portions are typically at least 25 nucleic acids or at least 8 amino acids.

The term "sequence identity" as used herein refers to the extent that sequences are identical on a nucleotide-by-nucleotide basis or an amino acid-by-amino acid basis over a window of comparison. Nucleic acid and protein sequence identities can be evaluated by using any method known in the art. For example, the identities can be evaluated by using the Basic Local Alignment Search Tool ("BLAST"). The BLAST programs identity homologous sequences by identifying similar segments between a query amino or nucleic acid sequence and a test sequence which is preferably obtained from protein or nuclei acid sequence database. The BLAST program can be used with the default parameters or with modified parameters provided by the user.

The term "percentage of sequence identity" is calculated by comparing two optimally aligned sequences over the window of comparison, determining the number of positions at which the identical nucleic acid base (e.g., A, T, C, G) or the identical amino acid residue (e.g., Ala, Pro, Ser, Thr, Gly, Val, Leu, lie, Phe, Tyr, Trp, Lys, Arg, His, Asp, Glu, Asn, Gln, Cys and Met) occurs in both sequences to yield the number of matched positions, dividing the number of matched positions by the total number of positions in the window of comparison (i.e., the window size), and multiplying the result by 100 to yield the percentage of sequence identity.

The term "substantial identity" of polynucleotide sequences means that a polynucleotide comprises a sequence that has at least 25% sequence identity. Alternatively, percent identity can be any integer from 25% to 100%. More preferred embodiments include at least: 25%, 30%, 35%, 40%, 45%, 50%, 55%, 60%, 65%, 70%, 75%, 80%, 85%, 86%, 87%, 88%, 89%, 90%, 91%, 92%, 93%, 94%, 95%, 96%, 97%, 98% or 99% compared to a reference sequence using the programs described herein; preferably BLAST using standard parameters, as described. These values can be appropriately adjusted to determine corresponding identity of proteins encoded by two nucleotide sequences by taking into account codon degeneracy, amino acid similarity, reading frame positioning and the like.

For peptides or proteins, the term "substantial identity" of amino acid sequences for purposes of this invention normally means polypeptide sequence identity of at least 40%. Preferred percent identity of polypeptides can be any integer from 40% to 100%. More preferred embodiments include at least 40%, 45%, 50%, 55%, 60%, 65%, 70%, 75%, 80%, 85%, 86%, 87%, 88%, 89%, 90%, 91%, 92%, 93%, 94%, 95%, 96%, 97%, 98%, 98.7%, or 99%.

Alternative Therapies for Patients with High Risk of Cancer Recurrence

For the purpose of this invention, an alternative therapy can be any kind of treatment different from the therapy that has been given to a patient subsequently identified with high risk of ovarian cancer recurrence. Alternative therapies also include re-treatment of the current therapies but with different dosages and/or combination with other therapeutic agents or administration arrangement. For example, alternative therapies include, but are not limited to, therapeutical treatments, immunotherapies, ayurvedic therapies, herbal therapies, dietary supplements, bioactive food components, unconventional pharmacological and biological interventions (e.g. antineoplastons, Coley's toxin, enzyme therapies, etc.), drugs/agents, biologies, radiation, heat, electroporation, surgery and physical exercise (e.g., yoga). Alternative therapies can be used as single therapy or in combination with other treatments.

In some embodiments, the alternative therapies of the present invention are augmented adjuvant therapies. Adjuvant therapy describes a way to target any remaining cancer cells after the primary cancer treatment, especially for the remaining cells that cannot be detectable. Typically, adjuvant therapies are the therapies used after primary treatments, such as surgery or radiation, to guard against cancer recurrences. The examples of adjuvant therapies include, but are not limited to chemotherapy, hormone therapy, radiation therapy and immunotherapy. More typically, adjuvant therapies in ovarian cancer platinum based and taxane based chemotherapy (e.g. cisplatin or carboplatin combined with paclitaxel). Patients who recur early (within six months from the end of adjuvant therapy) are considered platinum resistant; those recurring later than six months are referred to as platinum sensitive.

Following recurrence, platinum sensitive patients are often given a second round of a platinum and taxane based chemotherapy. Platinum resistant patients might also be given a second round, but often other kind therapy is added, or used without platinum and taxane.

In some specific embodiments, the alternative therapies are targeted molecular treatments, selected from the L01XC ATC class which includes, but is not limited to L01XC01 Edrecolomab, L01XC02 Rituximab, L01XC03 Trastuzumab, L01XC04 Alemtuzumab, L01XC05 Gemtuzumab, L01XC06 Cetuximab, L01XC07 Bevacizumab, L01XC08 Panitumumab, L01XC09 Catumaxomab, L01XC10 Ofatumumab, L01XC11 Ipilimumab, L01XC12 Brentuximab vedotin, and L01XC13 Pertuzumab. Preferably, the molecule treatment is L01XC07 Bevacizumab.

In some other specific embodiments, the alternative therapies are protein kinase inhibitors selected from the class L01XE, given that most of the NT6 compounds are ser-thre kinases and the receptors themselves are tyrosine kinases. The non-limiting examples of L01XE treatments include, but are not limited to, L01XE01 Imatinib, L01XE02 Gefitinib, L01XE03 Erlotinib, L01XE04 Sunitinib, L01XE05 Sorafenib, L01XE06 Dasatinib, L01XE07 Lapatinib, L01XE08 Nilotinib, L01XE09 Temsirolimus, L01XE10 Everolimus, L01XE11 Pazopanib, L01XE12 Vandetanib, L01XE13 Afatinib, L01XE14 Bosutinib, L01XE15 Vemurafenib, L01XE16 Crizotinib, L01XE17 Axitinib, L01XE18 Ruxolitinib, L01XE19 Ridaforolimus, L01XE21 Regorafenib, L01XE22 Masitinib, and QL01XE91 Toceranib. Preferably, the protein kinase inhibitor treatment is L01XE03 Erlotinib or L01XE02 Gefitnib.

In some embodiments, alternative therapies are salvage chemotherapies. For example, for patients resistant to primary therapy and have shown tumor growth during treatment, alternative therapies may include secondary non-cross resistant chemotherapies or other biological therapies. For patients who respond well to initial chemotherapy, who develop recurrent cancer within months after the end of primary care, or who showed a good response to primary chemotherapy and did not develop recurrent cancer for more than 6 months after the end of primary treatment, alternative therapies may include re-treatment and multiple re-treatments with a platinum-containing regimen. Alternative treatments can also be multiply combined, such as "doublet" and "triplet" treatment which is the accepted nomenclature for unspecified regimens involving multiple compounds or treatments.

Particularly, the more preferred alternative therapies for patients identified with high risk of ovarian cancer recurrence include, but are not limited to taxane, bevacizumab, docetaxel, doxorubicin (also referred to as PLD for pegylated liposomal doxorubicin), gemcitabine, pemetrexed, tamoxifen, and topotecan, and mixtures thereof. Further details are available at the website of the National Cancer Institute. These alternative therapies can be used as single therapy or in combination with other alternative or standard therapies. For example, the alternative therapies can be solo taxane treatments. The therapies can be platinum treatments with or without Taxol®, or latinum treatments with or without GEMZAR®, DOXIL®, or Topotecan.

Assays

Prediction of the present invention can be made on the basis of the detection of the presence, absence or extent of expression of the NT6 genes, including AKT2, KRAS, RAC1, CALM3, RPS6KA2, YWHAB or the gene products thereof in a patient.

Detection of the genes or their products may be carried out by any techniques known in the art. For example, the detection methods according to the invention include, but are not limited to, microarray, mass spectrometry, polymerase chain reaction (PCR), reverse transcription PCR, real-time PCR, in-situ hybridization, southern dot blots, immunoassay, ribonuclease protection assay cDNA array techniques, ELISA, protein, antigen or antibody arrays on solid supports such as glass or ceramics, small interfering RNA functional assays.

In some embodiments, the genes or the gene products of the invention can be detected by, for example, a probe or primer. The term "probe" as used herein refers to an oligonucleotide, polynucleotide or nucleic acid, either RNA or DNA, whether occurring naturally as in a purified restriction enzyme digest or produced synthetically, which is capable of annealing with or specifically hybridizing to a nucleic acid with sequences complementary to the probe. A probe may be either single-stranded or double-stranded. The exact length of the probe will depend upon many factors, including temperature, source of probe and use of the method. For example, for diagnostic applications, depending on the complexity of the target sequence, the oligonucleotide probe typically contains 15-25 or more nucleotides, although it may contain fewer nucleotides.

In some embodiments, the probes are selected to be complementary to different strands of one of the NT6 genes according their sequence. This means that the probes must be sufficiently complementary so as to be able to "specifically hybridize" or anneal with their respective target strands under a set of pre-determined conditions. Therefore, the probe sequence need not reflect the exact complementary sequence of the target. For example, a non-complementary nucleotide fragment may be attached to the 5' or 3' end of the probe, with the remainder of the probe sequence being complementary to the target strand. Alternatively, non-complementary bases or longer sequences can be interspersed into the probe, provided that the probe sequence has sufficient complementarities with the sequence of the target nucleic acid to anneal therewith specifically.

Thus, in a related aspect, the present invention provides methods of amplifying at least four of six target gene sequences comprising the steps of (a) providing a reaction mixture comprising a double-stranded target DNA, wherein the DNA is obtained from a subject, and (i) at least one pair of primers selected from the group designed to amplify at least four genes selected from the group consisting of target genes AKT2, KRAS, RAC1, CALM3, RPS6KA2 and YWHAB, wherein the primer pair comprises a first and a second primer that are complementary to the target DNA sequence, (ii) a polymerase and (iii) a plurality of free nucleotides comprising adenine, thymine, cytosine and guanine;

(b) heating the reaction mixture to a first predetermined temperature for a first predetermined time to separate the strands of the target DNA from each other;

(c) cooling the reaction mixture to a second predetermined temperature for a second predetermined time under conditions to allow the first and second primers to hybridize with their complementary sequences on the target DNA and to allow the polymerase to extend the primers; and (d) repeating steps (b) and (c) at least 10 times.

The term "primer" as used herein refers to an oligonucleotide, either RNA or DNA, either single-stranded or double-stranded, either derived from a biological system, generated by restriction enzyme digestion, or produced synthetically which, when placed in the proper environment, is able to functionally act as an initiator of template-dependent nucleic acid synthesis. When presented with an appropriate nucleic acid template, suitable nucleoside triphosphate precursors of nucleic acids, a polymerase enzyme, suitable cofactors and conditions such as a suitable temperature and pH, the primer may be extended at its 3' terminus by the addition of nucleotides by the action of a polymerase or similar activity to yield a primer extension product.

The primer may vary in length depending on the particular conditions and requirement of the application. In some embodiments of present invention, the oligonucleotide primer is at least 5 nucleotides in length, more preferably at least 10 nucleotides in length, more preferably at least about 15 nucleotides in length.

The primer must also be of sufficient complementarities to the desired template to prime the synthesis of the desired extension product, that is, to be able anneal with the desired template strand in a manner sufficient to provide the 3 hydroxyl moiety of the primer in appropriate juxtaposition for use in the initiation of synthesis by a polymerase or similar enzyme. It is not required that the primer sequence represent an exact complement of the desired template. For example, a non-complementary nucleotide sequence may be attached to the 5' end of an otherwise complementary primer. Alternatively, non-complementary bases may be interspersed within the oligonucleotide primer sequence, provided that the primer sequence has sufficient complementarities with the sequence of the desired template strand to functionally provide a template-primer complex for the synthesis of the extension product.

For the purpose of this invention, probes and primers are made to be complementary to the gene sequences of AKT2, KRAS, RAC1, CALM3, RPS6KA2, YWHAB or the substantially identical sequences thereof. The reagents of the kits of the present invention comprise the probes or primer complementary to at least four of these genes.

In some embodiments, the amplifying reaction comprises a series of repeated temperature changes or cycles, and preferably, a series of at least 10 times repeated cycles, with each cycle is preceded by a single temperature step (called hold) at a first predetermined temperature that is high enough to physically separated the two strands of the DNA double helix (DNA melting), and followed by one hold at the end for final product extension or brief storage where a second predetermined temperature is applied that is low enough for the two DNA strands to become templates for DNA polymerase to selectively amplify the target DNA gene.

The first and second pre-determined temperatures used and the length of time they are applied in each cycle depend on a variety of parameters, which includes, without limitation, the enzyme used for DNA synthesis, the concentration of divalent ions and dNTPs in the reaction, and the melting temperature of the primers. One skilled in the art would know how to select the primers and determine the temperatures and cycles for the amplification of the target DNA gene. In some embodiments, the cycle is repeated at least 5, 6, 7, 8 or 9, or preferably, at least 10 times.

The probes or the primers can also be labeled for the detection. Suitable labels, and methods for labeling primers are known in the art. For example, the label includes, without limitation, radioactive labels, biotin labels, fluorescent labels, chemiluminescent labels, bioluminescent labels, metal chelator labels and enzyme labels.

In some embodiments, the step (a) of the method further comprises adding a PCR reaction buffer and $MgCl_2$. The PCR reaction buffer and magnesium are either commercially available or readily prepared by one skilled in the art. The PCR reaction buffer and/$MgCl_2$ can be substituted by other suitable agents and chemicals known in the art.

In some embodiments, the method also comprises the step of analyzing the products of step (e) to determine whether increased risk of ovarian cancer in the subject is indicated, and/or to determine whether the products are predictive of increased resistance to platinum-based cancer therapies.

In some embodiments, the method additionally comprises the step of treating the subject with alternative therapies as described herein.

In some embodiments, the gene or the gene products of the invention can be detected by, for example, antibodies. Antibodies can be, for example, a natural or synthetic protein or fragment thereof, or nucleic acids (e.g., aptamers) with protein-binding or other antigen-binding characteristics. The antibodies will usually have a binding affinity for the peptide encoded by a gene described in the present invention. Preferably, the antibody is preferably specific to the peptide encoded by the genes of the invention, i.e. it binds with high affinity only to a specific peptide of the invention, and does not bind to other peptides. This allows the antibody to bind specifically to the peptide of the invention in a mixture containing a number of different peptides. The specific affinity of an antibody need not be for the entire molecular antigen, but for a particular site on it called the epitope.

The antibody may be of any suitable type, including monoclonal or polyclonal. Combinations of antibodies to two, three, four, five or more peptides encoded by the genes of the present invention are within the scope of the invention. The antibody may also be used without derivatization, or it may be derivatised with a cytotoxic agent such as radioisotope, enzyme, toxin, drug, pro-drug or the like.

The techniques for preparing and using various antibody-based constructs and fragments are well known in the art. Means for preparing and characterizing antibodies are also well known in the art. In some embodiments, the detection of the present invention can be achieved by using an antibody-based ELISA. The ELISA may include antibodies specific for antigens or epitopes of the gene products of the present invention. For an ELISA, antibodies can be produced in response to antigenic stimuli including, but not limited to, exposure to foreign proteins, microorganisms, and toxins. One of ordinary skill in the art can assess antigen-antibody immunocomplex formation by techniques commonly used in the art.

In some embodiments, the antibodies of the present invention are the antibodies raised against a peptide of any of the gene sequences of AKT2, KRAS, RAC1, CALM3, RPS6KA2, YWHAB or the substantially identical sequences thereof. The reagents of the kits of the present invention comprise antibodies for the peptides encoded by at least four of these genes. Preferably, the antibodies of the kits are used in an ELISA.

In another preferred embodiment, the expression of biomarkers of the present invention is detected by mass spectrometry, Multidimensional HPLC (High Performance Liquid Chromatography) can be combined with mass spectrometry to separate the biomarkers.

Also, the presence, absence or level of expression of the gene or gene product in the patient can be detected in vivo or in vitro. In some embodiments, expression is detected in vitro, in a biological sample containing genetic material that is isolated from the patient. In some other embodiments, expression of the marker gene can be carried out in vivo, for example using techniques such as "Quantum Dot" labeling or CT scan.

The following examples are offered for illustrative purposes only, and are not intended to limit the scope of the present invention in any way. Indeed, various modifications of the invention in addition to those shown and described herein will become apparent to those skilled in the art from the foregoing description and the following examples and fall within the scope of the appended claims.

EXAMPLES

To identify a clinically actionable biomarker of high-risk advanced ovarian cancer (AOC) patients, we applied the pathway-index model [3] to mRNA expression and survival data collected on ovarian cancer patients as part of the Cancer Genome Atlas (TCGA) project. For a given collection of genes specified a priori, the pathway-index model uses expression measured in a population of patients to identify susceptibility (resistance) genes conferring increased (decreased) risk of a time-to-event phenotype such as recurrence or death.

A patient-specific summary of risk, called an index, is then constructed using each patient's expression profile at the selected genes. After a search over 229 KEGG pathways [7], we identified an index from six genes (AKT2, KRAS, RAC1, CALM3, RPS6KA2, YWHAB) in the neurotrophin growth factor pathway (KEGG:hsa04722) whose overexpression is significantly associated with poor overall survival. We refer to the index hereinafter as NT6. The prognostic performance of NT6 to identify high-risk AOC patients is evaluated in two independent patient populations, and is shown to be comparable with leading approaches, using far fewer genes. Importantly, NT6 is also significantly associated with platinum resistance and identifies patients likely to respond to enhanced adjuvant therapy with high sensitivity and specificity, and thus may ultimately serve as a useful prognostic and predictive biomarker.

Results

NT6 summarizes signaling in the neurotrophin pathway. The signaling structure for the NT pathway shown in FIG. 1 highlights the position of the NT6 genes and their associated differentially expressed genes. FIG. 1 details 12 paths through the signaling layer (from the cytoplasm to nucleus) of which 9 contain at least one of the NT6 signaling genes, suggesting that NT6 provides a rather comprehensive summary of NT signaling. Furthermore, the NT6 genes have an unusually high betweenness measure [5] implying they are likely to be central to information low in this network ($p=0:025$).

NT6 predicts overall and progression-free survival in independent patient populations. To evaluate the ability of NT6 to predict overall survival, we compared its predictions of two classes (low-risk vs. high-risk) with two other prognostic signatures that were developed using the same TCGA data. The first marker developed by the TCGA Consortium [11] is based on expression from 193 genes and so we refer to it as TCGA193. The second, CLOVAR [13], uses 100 genes. These two markers outperform all methods to date with respect to predictive utility, including cytoreduction status. As valid assessment of any prognostic marker requires evaluation in independent datasets, we considered data from an additional 501 patients profiled in two independent studies. Although the TCGA data used to derive NT6, TCGA193, and CLOVAR is restricted to patients with stage III or IV serous ovarian adenocarcinomas, the independent studies we consider are more heterogeneous. Specifically, we considered 240 patients from Tothill et al. [12], a study conducted in Australia consisting of patients with ovarian, tubal, and peritoneal cancers; we also considered n=261 patients from Yoshihara et al. [14] conducted in Japan. In this independent population (referred to hereinafter as the 501 validation patients), NT6 shows predicative performance that is comparable to TCGA193 and CLOVAR (FIG. 2). NT6 also predicts progression-free survival (PFS) in this cohort (p=0.048). Taken together, these results indicate that NT6 may be a clinically useful prognostic marker for identifying AOC patients at high-risk for early recurrence or death.

Figure 3A:
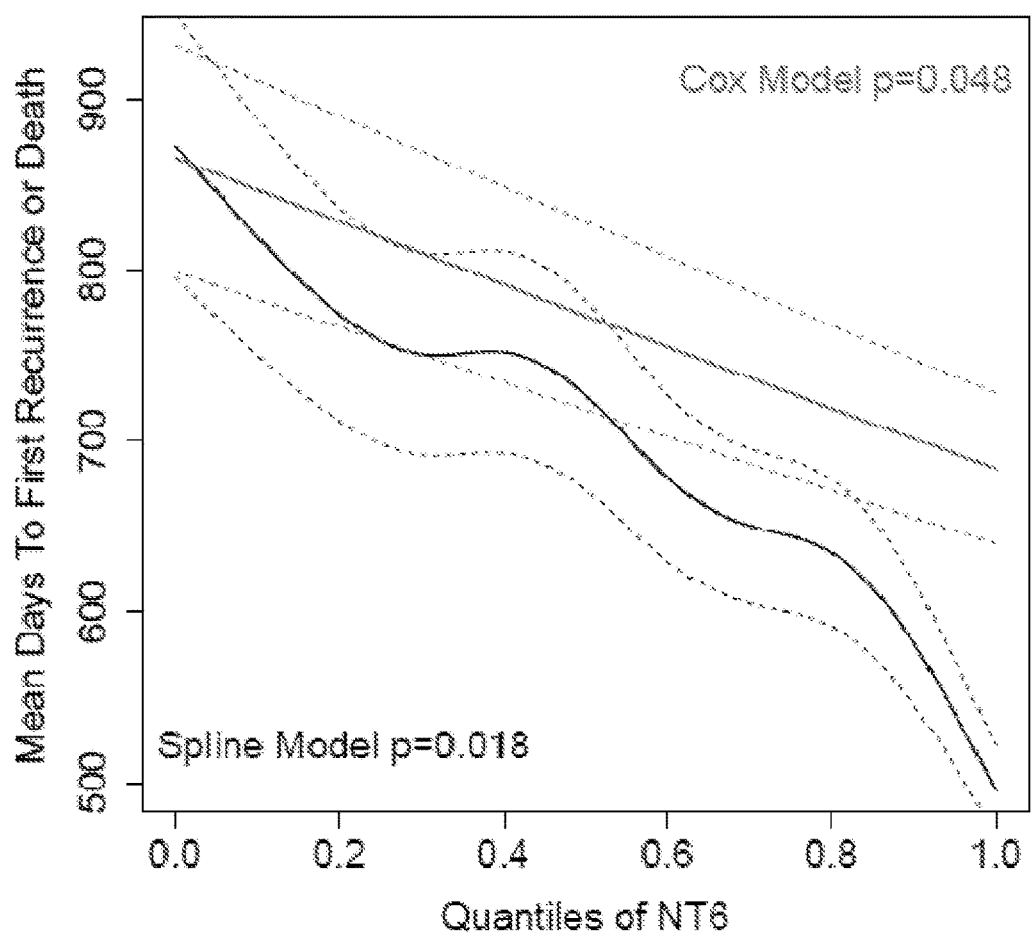
FIGS. 3A-3B show PFS for 501 validation patients as a function of NT6 quantiles (A) and PFS for 15 TCGA patients as a function of percent-change in NT6 (B). For these 15 patients, NT6 was measured in tumor tissue at diagnosis and at recurrence; a +5% change implies that NT6 was 5% higher at recurrence.
Figure 3B:
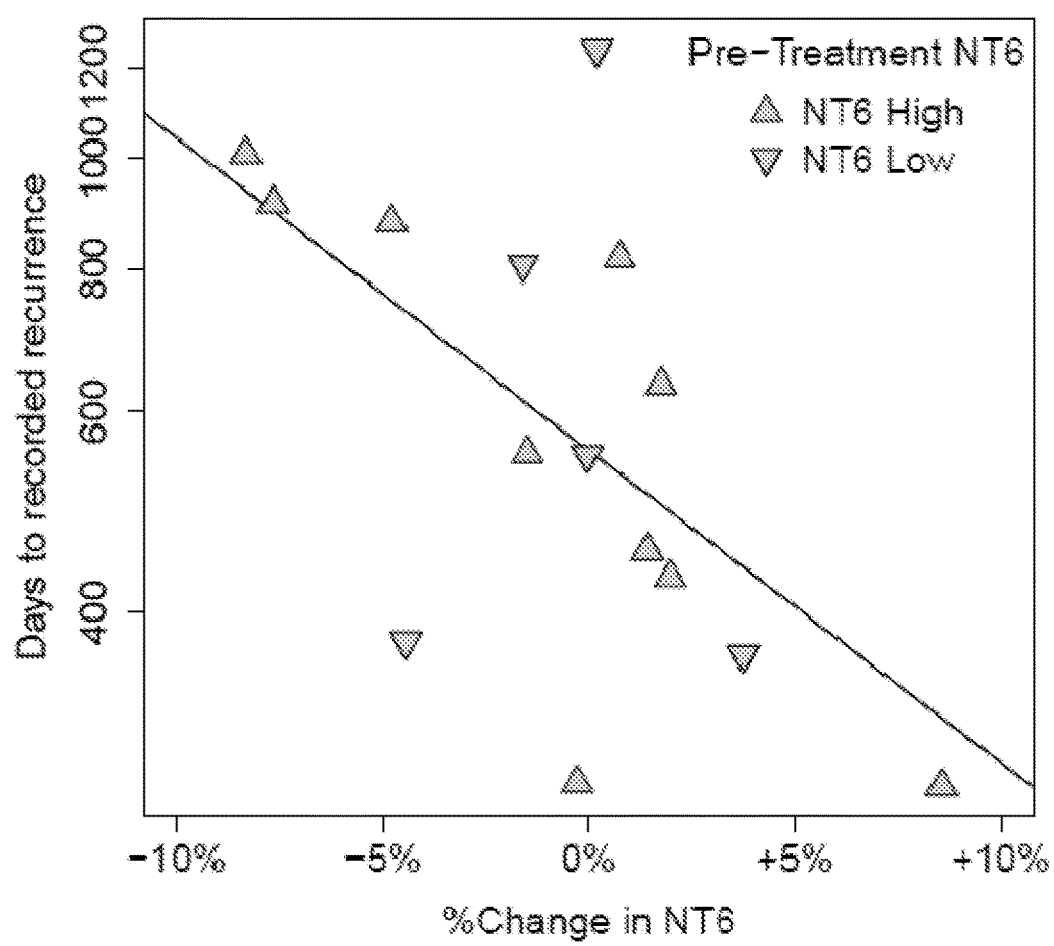

Increases in NT6 are associated with platinum resistance. Because adjuvant treatments for ovarian cancer are universally platinum-based, patients with short PFS times (<6 months after the end of adjuvant therapy) are referred to as platinum resistant. As noted in the previous section, NT6 accurately classifies patients into two PFS groups (low-risk vs. high-risk). We also investigated the clinical impact of continuous variation in NT6, as well as changes in NT6 over time. The left-panel of FIG. 3 shows the expected time to recurrence or death in the 501 validation patients estimated by a Cox regression model for all quantiles of NT6. The lowest levels of NT6 predict 874 days without further treatment while the highest levels predict 703 days (a difference of approximately 6 months); the non-linear fit suggests a greater difference. As the NT6 values considered thus far are derived from expression in the original tumor tissue, they provide no information on possible changes in this marker after chemotherapy.

The ability to assess the association between dynamic changes in NT6 and the development of platinum resistance in patient populations is limited since it is not common to biopsy recurrent tumor tissue. However, there are fifteen TCGA patients for which tumor tissue samples are available from both primary and recurrent tumors. The right panel of FIG. 3 shows PFS as a function of the percent change in NT6 for these patients (p=0.0224); median change was −0.03% with extremes−8.31% and +8.55%. The log-linear model predicts that a 1% increase in NT6 over time corresponds to a recurrence that is on average 33.9 days earlier (95% Cl:5.8-60.54). These results suggest that platinum has a shorter duration of efficacy for patients with high baseline NT6 (PFS is shorter) and that changes in NT6 are associated with accelerated or decelerated development of platinum resistance as assessed by time to first recurrence. To further investigate changes in NT6, we re-analyzed data from experiments where high-throughput expression was measured in ovarian cancer cell-lines exposed to platinum over time [8].

Enhanced adjuvant therapy may benefit at-risk patients. Since patients with high levels of NT6 are at increased risk for early recurrence, we investigated whether enhanced adjuvant therapy for these patients provided benefit. Of the 503 TCGA patients considered, we focused on 465 for which treatment information was available. Of these, 366 received standard of care for adjuvant therapy (platinum and paclitaxel only) and 99 received enhanced adjuvant therapy (an agent or combination of agents in addition to platinum and paclitaxel). Patients with high NT6 who received enhanced adjuvant therapy showed significantly longer PFS than expected.

Specifically, median PFS was decreased by 6.7 months in those high NT6 patients who received standard of care, but decreased by only 1.4 months in those high NT6 patients receiving enhanced therapy. The difference is statistically significant (p=0.037). These results suggest that NT6 may prove useful in identifying high-risk patients who would benefit from enhanced adjuvant therapy. To further investigate this possibility, we measured NT6 using qRT-PCR in 22 serous ovarian cancer patients at the Medical College of Wisconsin. Of these, 9 received standard of care and 13 received enhanced therapy. We see a 40% expected increase in risk with high NT6, and a 17% expected increase in risk in the enhanced group. For patients that are high NT6, receiving enhanced therapy is expected to decrease risk by 19 significant at p=0.05.

NT6 knock-down slows growth, but does not resensitize to platinum in OC cell lines. As NT6 is associated with the development of platinum resistance, we investigated the potential of NT6 to serve as a drug target on its own, and of NT6 knockdown to resensitize a patient to platinum. Toward this end, we conducted a set of cell line experiments measuring cell proliferation in A2780, A2780cis, OVCAR, and SKOV3 cell lines following knock-down of the NT6 genes. Similar experiments were conducted by assessing proliferation following platinum; no differences were observed. Taken together, these results imply that NT6 knock down may serve as a useful therapeutic target that slows tumor growth, but does not resensitize a tumor to platinum treatment.

NT6 related somatic mutation burden confers transient effect on survival. In addition to expression-based prognoses via NT6, we considered the influence of related somatic mutations on survival. Within each gene in the NT pathway, we calculated the somatic burden as the proportion of somatic mutations within that gene. By BIC stepwise selection over all burden variables, we found that mutations in 6 genes (BDNF, IRAK1, KRAS, PRDM4, RAC1, RPS6KA2) explained 18% of variation in NT6; three of the genes (RAC1, RPS6KA2, KRAS) are in the NT6 signature while three (BDNF, IRAK1, and PRDM4) are not. No burden statistics were associated with survival on their own, but the joint model was strongly associated (p=0.001). Early on, a low burden of somatic mutations is mildly protective, but this effect disappears by 60 months.

Figure 4:
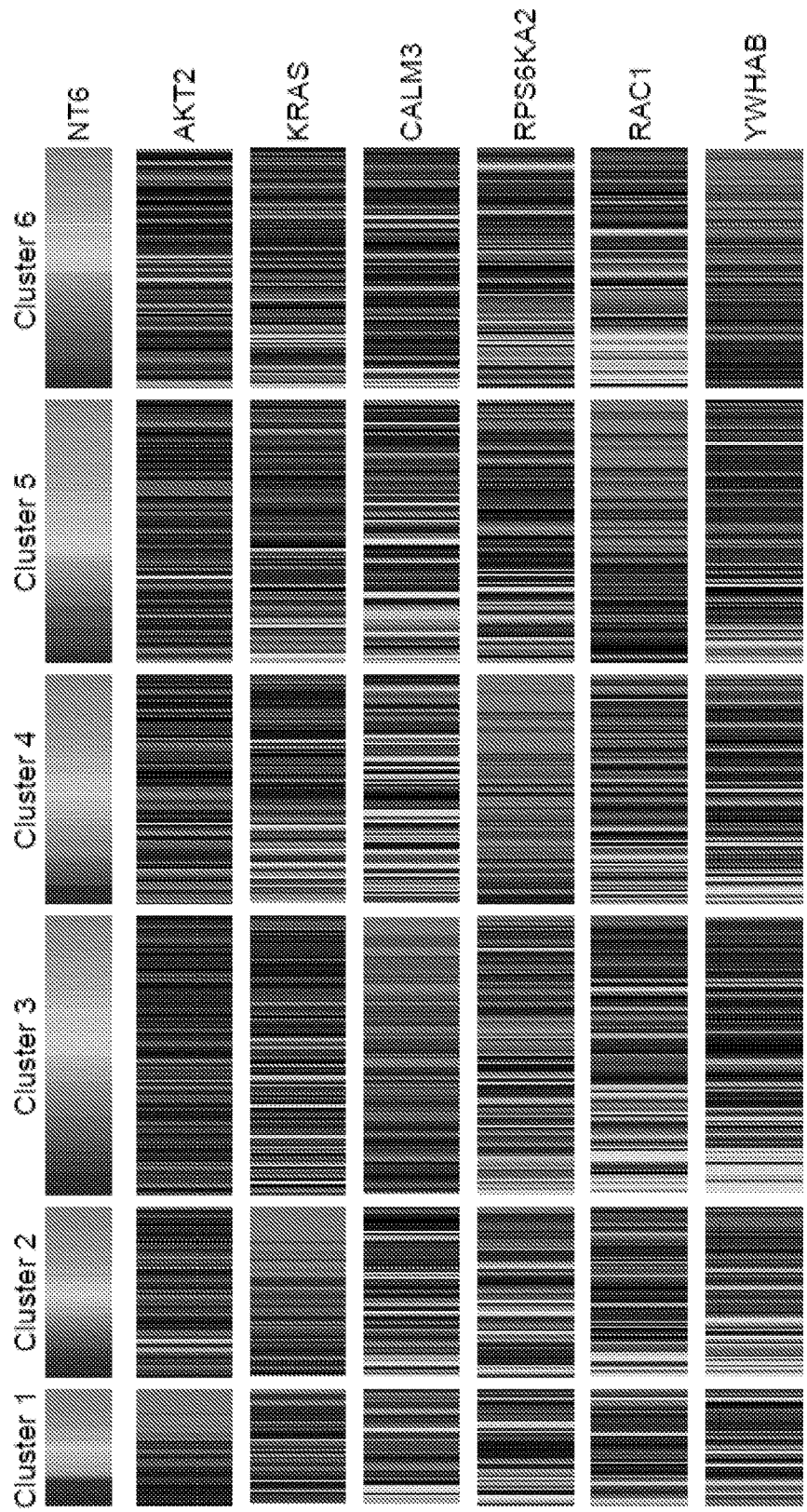
FIG. 4 shows hierarchical clustering stratifies the 503 TCGA patients into six groups, shown in columns; expression of the six genes is shown in the rows. After the six clusters were defined, patients within each cluster were ordered by average NT6 shown in the top row from low (blue) to high (pink).
Figure 5:
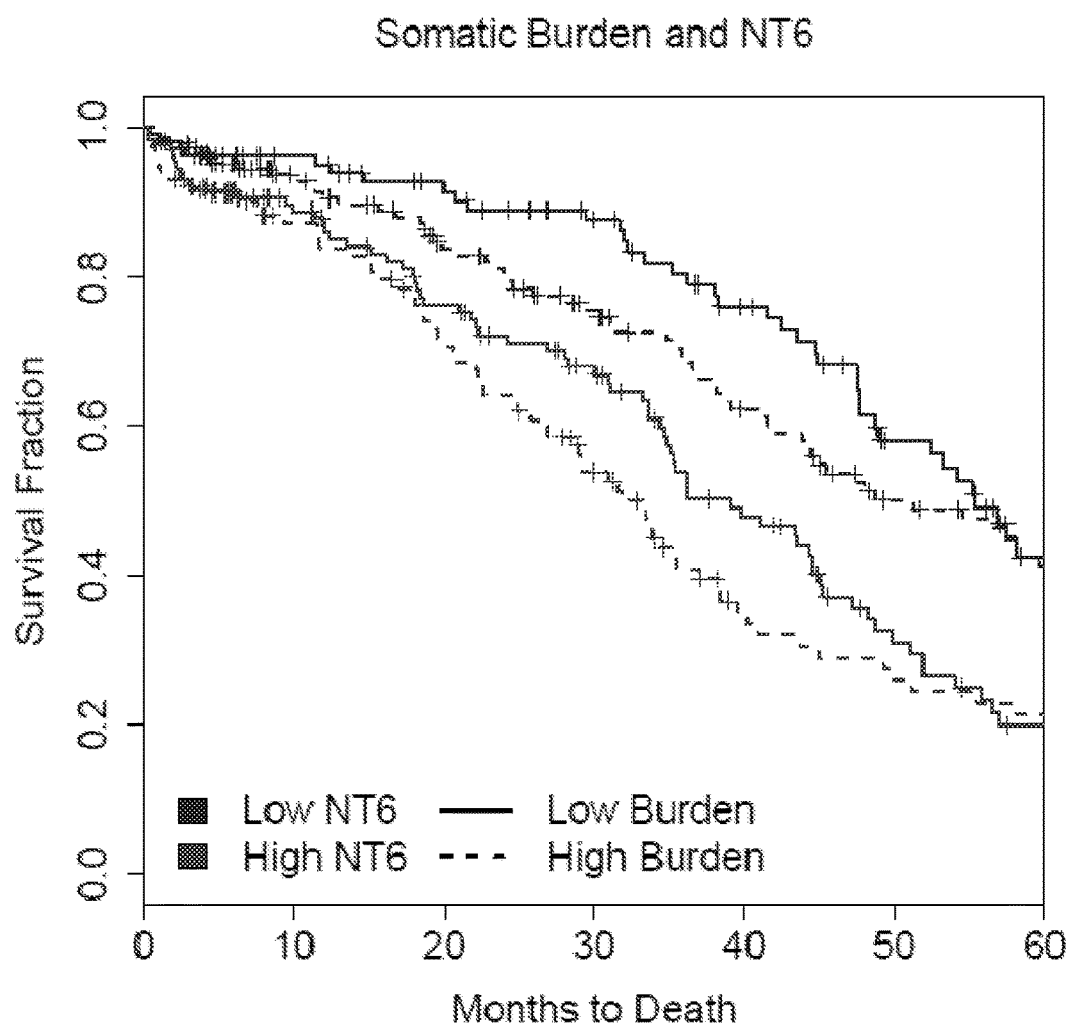
FIG. 5 shows Kaplan-Meier curves showing percent survival for 503 TCGA patients stratified into four groups defined by NT6 (low vs. high) and somatic mutation burden (low vs. high). The 501 validation patients are not shown since genotype data is not available for these patients.

NT6 stratifies patients into meaningful groups that show differential response to treatment. Since high levels of NT6 are associated with adverse outcomes, we investigated the relative contributions of each of the six genes comprising NT6 to see if the signal was largely driven by one, or a few, genes in most patients. FIG. 4 shows the 503 TCGA patients clustered by expression across the six NT6 genes. The patients separate into seven groups, with each group showing a distinct expression signature. Patients in the first group, for example, have relatively high expression of AKT2; patients in the second group have relatively high expression of KRAS. Furthermore, each group contains high NT6 patients indicating that high NT6 is not driven by a single factor common across patients.

Discussion

We have used the pathway-index model to identify NT6, a six-gene mRNA based prognostic and predictive biomarker for guiding treatment in advanced ovarian cancer patients. The marker was derived using data from the TCGA ovarian project, and validated in independent patient populations.

The PIM starts with pathways for two main reasons. The first is that there is a wealth of information available in cancer-related pathways. Vogelstein tells us this. Why not use it. Second is Jones et al. Much more consensus at the pathway level.

Our results demonstrate that NT6 provides for accurate ovarian cancer patient prognosis that significantly improves the prognosis provided by the clinical variables in use today (e.g. cytoreduction, age, stage and grade). Furthermore, we have demonstrated that patients identified as high-risk by NT6 have significantly improved progression-free survival times if treated early on with an enhanced adjuvant therapy. This suggests that NT6 may prove immediately useful in guiding treatment.

The results presented here also suggest that NT6 itself may serve as a drug target in improved therapies. Specifically, ovarian cancer cell-line experiments demonstrate that NT6 knock down results in a significant decrease in cell proliferation. As high NT6 is associated with the development of platinum resistance, we also investigated whether knock down would resensitize ovarian cancer cell-lines to platinum, but no advantage was observed. Taken together, our results imply that NT6 is identifying fast growing tumors, but not necessarily those that are most resistant to platinum.

In addition to NT6 baseline providing useful information at the time of surgery, the results presented here demonstrate that changes in NT6 levels are also clinically relevant. By analyzing NT6 in patients for which tumor tissue was available at both diagnosis and recurrence, we demonstrated that increases in NT6 are significantly associated with earlier recurrence, which suggests that NT6 may ultimately be useful in patient monitoring over time. In addition, our results show that high NT6 patients benefit from enhanced adjuvant therapy.

Online Methods

Expression Data Cohorts. Expression and clinical data were obtained from the TCGA Data Portal consistent with public data use requirements. Data for validation studies were obtained from the gene expression omnibus, GEO: (G5E9891 and G5E32062). Affymetrix U133A arrays were selected when possible. The GEO GPL annotation files were used to align probes to genes across all studies. We considered 251 patients from Tothill et al. [12], a study conducted in Australia consisting of patients with ovarian, tubal, and peritoneal cancers; we also considered n=250 patients from Yoshihara et al. [14] conducted in Japan, for a total of 501 patients in the validation data set. Further detail is provided below. Data from [8] was downloaded from GEO (GSE: 23603) to investigate NT6 expression during induced platinum resistance experiments in ovarian cancer cell lines. For all gene expression datasets, robust multi-array analysis [6] was used for normalization.

Pathway Index Modeling. KEGG annotations were obtained using the R package hthgu133a.db.2.5.0 available at Biconductor website; 229 KEGG pathways were considered. For each pathway, we used the pathway index model described in [3] to identify susceptibility and resistance genes associated with overall survival; the difference between average expression of the susceptibility genes and average expression of the resistance genes defines the so-called pathway index. For training the models, we use the designated TCGA—training cohort and survival truncated at 60 months to minimize the effect of long-term survivors. For 168 of 229 pathways, at least one gene was selected so a pathway index could be calculated.

Using the three validation sets separately, we tested the association between the predicted indexes and overall survival. Dichotomizing the predicted scores, we note that only Neurotrophin (NT) signaling (KEGG:hsa04277) is significant in all three validation sets and the TCGA testing set. While the VEGF signal (KEGG:hsa04370) is more significant in the TCGA Test set, it is not significant in two of the validation sets and half of its genes overlap with other pathways. In contrast, the genes selected are highly specific to NT signaling suggesting robustness of function and minimal overfitting.

NT6 Signaling and Differential Expression Analysis. We computed the average betweenness of the 6 NT6 genes given their relative positions in the KEGG structured graph. The betweenness score provides a measure of the volume of information that passes through these genes, with high scores indicating critical pathways within a network [4]. We compared the observed score to scores obtained by randomly sampling sets of 6 genes within the pathway; 1000 random samples were considered. Patients are defined as having high NT6 expression if their NT6 expression is in the top 40% (above the 60th quantile). Genes differentially expressed between low NT6 and high NT6 patients were identified using Students' t-test. Bonferroni adjusted p-values are reported.

Survival Analysis. Comparisons between pairs of survival curves were conducted using the log-rank test. Paired Sample Analysis. Eighteen TCGA samples are listed as recurrent solid tumor tissue. Of these, 15 had matched primary tumor tissue samples and we aligned the Tier 3 TCGA expression data for all of these arrays. Because all of these patients recurred and were re-biopsied, we regressed the time to first recurrence by the relative change in NT6 signal. The result was a significant negative association ($p=0.0224$) between the increase in NT6 and PFS.

Assessment of Enhanced Adjuvant Therapies. Treatment information available in the TCGA includes dates bounding the beginning and end of a treatment regimen. Adjuvant treatment vs. treatment for recurrence is also specified. Treatment information was available for 214 TCGA ovarian cancer patients. With few exceptions, each patient received a platinum based chemotherapy (cisplatinum or carboplatinum) combined with paclitaxel for adjuvant therapy. In addition to platinum and paclitaxel, 99 patients also received an additional agent(s) for adjuvant. We refer to these patients as receiving enhanced adjuvant therapy.

Cell Lines. The A2780 and A2780cis cell lines were purchased from Sigma-Aldrich. The NIH:OVCAR-3 and SKOV3 cell lines were purchased from ATCC. The A2780 and A2780cis cell lines were cultivated in Gibco RPMI-1640 media (Life Technologies), supplemented with 10% (v/v) of Fetal Bovine Serum (FBS; Hyclone) and 1% Gibco Penicillin-Streptomycin (PS; Life Technologies). The NIH:OVCAR-3 cell line was cultivated in RPMI-1640 media, supplemented with 20% of FBS and 1% PS. The SKOV-3 cell line was cultivated in McCoys 5a modified media (ATCC), supplemented with 10% FBS and 1% PS. All cell lines were cultivated at 37C under 5% atmospheric $CO_2$.

Transfections with siRNAs. The cell lines were transiently transfected with siRNAs against the 6 NT6 genes or with the same concentration of the non-targeting pool siRNAs (Dharmacon). The transfections were done using Lipofectamin 2000 (Life Technologies) in 24-well plates, following the manufacturers recommendations. The transfection mixtures for single or equivalent concentration of the non-targeting pool siRNAs contained 1 l of Lipofectamin 2000 reagent, 100 nM of siRNA in 500 l of Gibco Opti-MEM (Life Technologies). For simultaneous transfection with siRNAs directed to multiple genes, the mixtures contained 2 l of Lipofectamin 2000 reagent, 50 nM of each siRNA (up to 300 nM of total siRNA) in a total of 500 l of Opti-MEM. The transfection mixtures were replaced by culture media after 5-6 h incubation. Transfected cells were harvested for experimental procedures 48 h after transfection.

Proliferation Assay by BrdU Incorporation. A total of 5,000 transfected cells were re-plated in each well of a 96-well plate. The cells were allowed to settle for minimally 4 h. Bromodeoxyuridine (BrdU) was added at the dose recommended by the BrdU assay kits manual (Roche Applied Sciences). BrdU was washed off after 17 h and the level of BrdU incorporation as a surrogate for proliferation, was determined by ELISA (following the kits manual). At least 3 replicates per transfection condition were assayed on each 96-well plate. The data were normalized against the average of the non-targeting pool transfection condition assayed on the same plate.

Quantitative Real-Time PCR. A fraction of the cells was saved for analysis of gene expression. The cells were pelleted, washed in cold sterile PBS and lysed by vigorous pipetting in 350 l of RNA lysis buffer from the QiaGen RNA extraction kit that was further used for RNA extraction. To synthesize cDNA from 700 ng of TURBO-free DNaseI-treated total RNA, the reverse transcriptase Superscript II kit (LifeTechnologies) was used according to manufacturers directions. Quantitative real-time PCR (QPCR) was used to quantify transcript levels. TaqMan quantitative PCR primers and probes were ordered as premade assays (ABI/Applied Biosystems). Reactions were run on a ABI-7900 RT-PCR system. Quantities of transcripts were measured by comparison of Ct values with a standard curve calculated from serial dilutions made from reverse transcriptase reactions that contained 2 g of total RNA. Sample measurements are an average of two or three replicates within 0.5 Ct value. Sample measurements were normalized by dividing the gene specific transcript quantity over the ActB endogenous control quantity. For each sample, the ratio was scaled to the average ratio of the non-targeting pool sample group from the same experiment.

Heterogeneity and Assessment of Treatment Response. Patients are defined as having high NT6 expression if their NT6 expression is in the top 40% (above the 60th quantile). The set of genes driving the NT6 average above the 60th quantile varies from patient to patient (FIG. 4) and we subdivide patients into categories using their maximally expressed gene.

Somatic Mutation Data. Affymetrix SNP6.0 data were obtained from the TCGA Data Portal and genotypes were called with Birdseed 2.0. Patients were matched to their normal tissue arrays and a somatic mutation was recorded if the genotype changed between normal and tumor samples. Burden statistics are the sum of genotype changes across all SNPs associated with a gene. Associations are taken from the Affymetrix SNP6.0 annotation database.

Expression Data Cohorts. Expression and clinical data were obtained from the TCGA Data Portal (http://cancergenome.nih.gov), consistent with public data use requirements. Patient records were available for 516 patients. We considered expression assayed using the Affymetrix HGU133A platform. We dropped 13 patients who had no survival times, leaving 503 patients. Data for the validation studies were obtained from the gene expression omnibus, GEO: GSE9891 (285 samples) and GSE32062 (270 samples). GSE9891 provides expression measured using the Affymetrix HG-U133Plus2 platform. We kept the subset of probes that lined up (by probe name) with the TCGA data. Clinical data was obtained from the supplement to Tothill et al. [12] (it was not available at GEO). We aligned the expression and clinical data by matching the GSM numbers to the tagged names in the spreadsheet manually. Following the TCGA study [1], we eliminate low malignant potential and Stage I tumors. A further 7 tumors lack survival information leaving 240 arrays. It should be noted that some of these array non-ovary tissue, treatments vary and the type/histology of ovarian cancer varies. The inclusion of these other arrays facilitates comparisons with other studies, but attenuates the validation signal, providing results that are somewhat conservative and likely more realistic.

REFERENCES

1. D. Bell, et al., Integrated genomic analyses of ovarian carcinoma. Nature, 474(7353):609-615, June 2011.
2. A. H. Bild, et al., Oncogenic pathway signatures in human cancers as a guide to targeted therapies. Nature, 439(7074):353-357, January 2006.
3. Kevin H Eng, et al., Pathway index models for construction of patient-specific risk profiles. Statistics in Medicine, 32(9):1524-1535, 2012.
4. L. C. Freeman. A set of measures of centrality based on betweenness. Sociometry, 40:35-41, 1977.
5. [5] Linton C Freeman. A set of measures of centrality based on betweenness. Sociometry, 40(1):35-41, 1977.
6. R. A. Irizarry, et al., Speed. Exploration, normalization, and summaries of high density oligonucleotide array probe level data. Biostatistics, 4(2):249-264, April 2003.
7. M. Kanehisa and S. Goto. KEGG: Kyoto encyclopedia of genes and genomes. Nucleic Acids Research, 28(1):27-30, 2000.
8. D. C. Marchion, et al., BAD phosphorylation determines ovarian cancer chemosensitivity and patient survival. Clin. Cancer Res., 17(19):6356-6366, October 2011.
9. Rosalind A Segal. Selectivity in neurotrophin signaling: theme and variations. Annual review of neuroscience, 26(1):299-330, 2003.
10. R. Siegel, et al., Cancer statistics, 2013. CA Cancer J Clin, 63(1):11-30, January 2013.
11. The Cancer Genome Atlas Research Network. Integrated genomic analyses of ovarian carcinoma. Nature, 474:609-615, 2011.
12. Richard W Tothill, et al. Novel molecular subtypes of serous and endometrioid ovarian cancer linked to clinical outcome. Clinical Cancer Research, 14(16):5198-5208, 2008.
13. Roel G W Verhaak, et al. Prognostically relevant gene signatures of high-grade serous ovarian carcinoma. The Journal of Clinical Investigation, 123(1):517, 2013.
14. Kosuke Yoshihara, et al. Gene expression profile for predicting survival in advanced-stage serous ovarian cancer across two independent datasets. PloS one, 5(3):e9615, 2010.

We claim:

1. A method of treating a subject having ovarian cancer, the method comprising the steps of:
    (a) obtaining a first sample from the subject prior to treatment for ovarian cancer,
    (b) measuring the expression level of AKT2, KRAS, RAC1, and CALM3 in the sample from (a),
    (c) obtaining a second sample from the subject after treatment for ovarian cancer,
    (d) measuring the expression level of AKT2, KRAS, RAC1, and CALM3 in the sample from (c),
    (e) detecting an increased level of expression of the genes in the second sample, as compared to the level of expression of the genes in the first sample, wherein the increased level of expression is at least 1%,
    (f) diagnosing the subject as in need of alternative therapy, and
    (g) administering to the diagnosed subject an alternative therapy selected from the group consisting of taxane, bevacizumab, docetaxel, doxorubicin, gemcitabine, pemetrexed, tamoxifen, topotecan, and mixtures thereof.

2. The method of claim 1 wherein the treatment for ovarian cancer is platinum based chemotherapy.

3. The method of claim 1 wherein the alternative therapy is administered with platinum.

4. The method of claim 1 wherein the alternative therapy is used without platinum.

5. A method for reducing the risk of recurrence in a subject having ovarian cancer, the method comprising the steps of:
    (a) obtaining a first sample from the subject prior to treatment for ovarian cancer,
    (b) measuring the expression level of AKT2, KRAS, RAC1, and CALM3 in the sample from (a),
    (c) obtaining a second sample from the subject after treatment for ovarian cancer,
    (d) measuring the expression level of AKT2, KRAS, RAC1, and CALM3 in the sample from (c),
    (e) detecting an increased level of expression of the genes in the second sample, as compared to the level of expression of the genes in the first sample, wherein the increased level of expression is at least 1%,
    (f) diagnosing the subject as being at risk of recurrence of ovarian cancer, and
    (g) administering to the diagnosed subject an alternative therapy selected from the group consisting of taxane, bevacizumab, docetaxel, doxorubicin, gemcitabine, pemetrexed, tamoxifen, topotecan, and mixtures thereof.

6. The method of claim 5 wherein the treatment for ovarian cancer is platinum based chemotherapy.

7. The method of claim 5 wherein the alternative therapy is administered with platinum.

8. The method of claim 5 wherein the alternative therapy is used without platinum.

9. The method of claim 1, wherein the alternative therapy is taxane.

10. The method of claim 5, wherein the alternative therapy is taxane.

* * * * *

UNITED STATES PATENT AND TRADEMARK OFFICE
CERTIFICATE OF CORRECTION

PATENT NO. : 10,167,516 B2
APPLICATION NO. : 15/339109
DATED : January 1, 2019
INVENTOR(S) : Christina Kendziorski Newton et al.

Page 1 of 1

It is certified that error appears in the above-identified patent and that said Letters Patent is hereby corrected as shown below:

In the Specification

Column 9, Line 55, "25% 50% 0% 5% 80%" should be --25%, 50%, 70%, 75%, 80%--.

Column 18, Line 39, "(G5E9891 and G5E32062)" should be --(GSE9891 and GSE32062)--.

Signed and Sealed this
Twenty-sixth Day of February, 2019

Andrei Iancu
*Director of the United States Patent and Trademark Office*